United States Patent [19]

Zimmerman et al.

[11] Patent Number: 4,992,450

[45] Date of Patent: Feb. 12, 1991

[54] PIPERIDINE OPIOID ANTAGONISTS

[75] Inventors: Dennis M. Zimmerman, Mooresville; Charles H. Mitch, Indianapolis, both of Ind.

[73] Assignee: Eli Lilly and Company, Indianapolis, Ind.

[21] Appl. No.: 448,800

[22] Filed: Dec. 11, 1989

Related U.S. Application Data

[60] Division of Ser. No. 284,504, Dec. 14, 1988, Pat. No. 4,891,379, which is a continuation of Ser. No. 39,121, Apr. 16, 1987, abandoned.

[51] Int. Cl.$^5$ ............................................. A61K 31/445
[52] U.S. Cl. ..................................................... 514/315
[58] Field of Search .......................................... 514/315

[56] References Cited

U.S. PATENT DOCUMENTS

| | | | |
|---|---|---|---|
| 3,991,199 | 11/1976 | Berger | 546/86 |
| 4,141,980 | 2/1979 | Berger | 546/87 |
| 4,191,771 | 3/1980 | Zimmerman | 424/267 |
| 4,581,456 | 4/1986 | Barnett | 546/185 |

OTHER PUBLICATIONS

Leander et al., *European Journal of Pharmacology* 81, 185–192.
Leander et al., *Drug Development Research* 4: 421–427 (1984).
Baile et al., *Physiology & Behavior*, vol. 26, 1019–1023 (1981).
Zimmerman et al., *Nature*, vol. 275, Sep. 28, 1978, pp. 332–334.
Leander, The Journal of *Pharmacology and Experimental Therapeutics*, vol. 224, No. 1, 89–94 (1983).

*Primary Examiner*—Stanley J. Friedman
*Attorney, Agent, or Firm*—David E. Boone; Joseph A. Jones; Leroy Whitaker

[57] ABSTRACT

This invention provides trans-3,4 1-substituted-3-substituted-4-methyl-4-(3-substituted phenyl)piperidines as opioid antagonists capable of blocking the mu or kappa receptors in the brain.

26 Claims, No Drawings

PIPERIDINE OPIOID ANTAGONISTS

This application is a division, of application Ser. No. 07/284,504, filed Dec. 14, 1988, now U.S. Pat. No. 4,891,379, which is a continuation of Ser. No. 07/039,121, filed Apr. 16, 1987, now abandoned.

SUMMARY OF THE INVENTION

The present invention relates to a trans-3,4 isomer of a compound of the formula

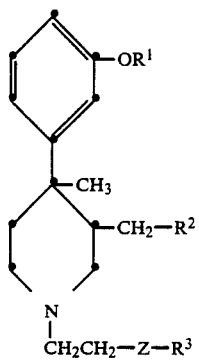

I wherein:
$R^1$ is hydrogen or $C_1$-$C_4$ alkanoyl;
$R^2$ is hydrogen, $C_1$-$C_4$ alkyl or $C_2$-$C_6$ alkenyl;
$R^3$ is $C_4$-$C_8$ cycloalkyl, $C_4$-$C_8$ cycloalkenyl, $C_1$-$C_6$ alkyl, $C_2$-$C_6$ alkenyl, $C_1$-$C_4$ alkyl substituted $C_4$-$C_8$ cycloalkyl, $C_1$-$C_4$ alkyl substituted $C_4$-$C_8$ cycloalkenyl or thiophene;
Z is

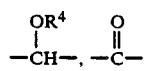

or a bond;
$R^4$ is hydrogen, $C_1$-$C_6$ alkyl,

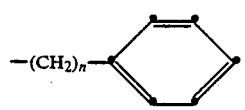

or

$R^5$ is $C_1$-$C_4$ alkyl or

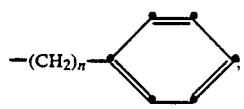

n is 1, 2 or 3; and the pharmaceutically acceptable salts thereof.

The present invention also provides methods of employing, and pharmaceutical formulations containing, a compound of the invention.

DETAILED DESCRIPTION OF THE INVENTION

The term "$C_1$-$C_4$ alkanoyl", as used herein, represents an alkanonyl group having from one to four carbon atoms. Typical $C_1$-$C_4$ alkanoyl groups include acyl, propanoyl, butanoyl and the like.

$C_4$-$C_8$ Cycloalkyl represents cyclobutyl, cyclopentyl, cyclohexyl, cycloheptyl and cyclooctyl.

$C_4$-$C_8$ Cycloalkenyl includes cyclobutenyl, cyclopentyl, cyclohexenyl, cycloheptenyl, cyclooctenyl and the like.

$C_1$-$C_6$ Alkyl includes methyl, ethyl, n-propyl, isopropyl, n-butyl, sec-butyl, n-pentyl, neopentyl, n-hexyl, isohexyl, and the like.

$C_2$-$C_6$ Alkenyl includes vinyl, allyl, 3-butenyl, 3-methyl-2-butenyl,2,3-dimethyl-2-butenyl, and the like.

$C_1$-$C_4$ Alkyl substituted $C_4$-$C_8$ cycloalkyl represents a $C_4$-$C_8$ cycloalkyl group having one or more $C_1$-$C_4$ alkyl substituents. Typical $C_1$-$C_4$ alkyl substituted $C_4$-$C_8$ cycloalkyl groups include cyclobutylmethyl, 2-cyclobutylpropyl, (2-methylcyclobutyl)methyl,2-cyclohexylethyl, and the like.

$C_1$-$C_4$ Alkyl substituted $C_4$-$C_8$ cycloalkenyl represents a $C_4$-$C_8$ cycloalkenyl group having one or more $C_1$-$C_4$ alkyl groups. Typical $C_1$-$C_4$ alkyl substituted $C_4$-$C_8$ cycloalkenyl groups include cyclobutenylmethyl, cyclopropenylethyl, (2-ethylcyclohexenyl)methyl, and the like.

$C_1$-$C_6$ Alkoxy represents a straight or branched alkoxy chain having from one to six carbon atoms. Typical $C_1$-$C_6$ alkoxy groups are methoxy, ethoxy, n-propoxy, isopropoxy, n-butoxy, n-propoxy and the like.

"Halo" or "halogen" represents fluoro, chloro, bromo or iodo.

Thiophene means 2-thiophene or 3-thiophene.

While all of the compounds of the present invention are useful opioid antagonists, certain of the present compounds are preferred for that use. Preferably, Z is

$R^1$ $R^2$ and $R^4$ are hydrogen, and $R^3$ is $C_4$-$C_8$ cycloalkyl, and especially cyclohexyl. Also, the compounds preferably exist as pharmaceutically acceptable salts. Other preferred aspects of the present invention will be noted hereinafter.

The piperidines of the invention as illustrated in formula I occur as the trans stereochemical isomers by virtue of the substituents at the 3- and 4-positions. More specifically, the alkyl or alkenyl group at the 3-position is situated in a trans position relative to the methyl group at the 4-position. As such, the compounds can exist as the trans (+) isomer of the formula

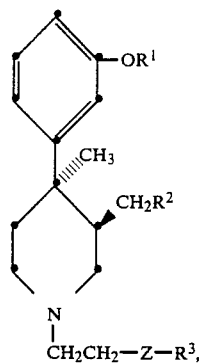

or the trans (−) isomer of the formula

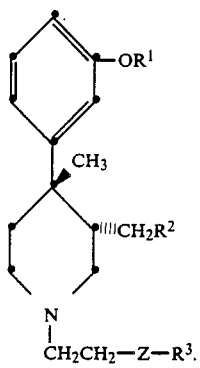

The present invention comtemplates both the individual trans (+) and (−) stereoisomers, as well as the racemic mixture of the trans stereoisomers.

Also, when Z is

the carbon atom attached to the $OR^4$ group is asymmetric. As such, this class of compounds can further exist as the individual R or S stereoisomers, or the racemic mixture of the isomers, and all are contemplated within the scope of the compounds of the present invention.

The piperidines of this invention form pharmaceutically acceptable acid addition salts with a wide variety of inorganic and organic acids. The particular acid used in salt formation is not critical; however, the corresponding salt that is formed must be substantially nontoxic to animals. Typical acids generally used include sulfuric, hydrochloric, hydrobromic, phosphoric, hydroiodic, sulfamic, citric, acetic, maleic, malic, succinic, tartaric, cinnamic, benzoic, ascorbic, and related acids. The piperidines additionally form quaternary ammonium salts with a variety of organic esters of sulfuric, hydrohalic and aromatic sulfonic acids, and the like. Among such esters are methyl chloride, ethyl bromide, propyl iodide, butyl bromide, allyl iodide, isobutyl chloride, benzyl bromide, dimethyl sulfate, diethyl sulfate, methyl benzensulfonate, ethyl toluenesulfonate, crotyl iodide, and the like.

The compounds of the present invention may be prepared by a variety of procedures well known to those of ordinary skill in the art. The preferred procedure involves the reaction of a 3-substituted-4-methyl-4-(3-substituted phenyl)piperidine with an appropriate acylating agent to provide the corresponding intermediate, which is reduced to the compound of the present invention under standard conditions. This reaction may be represented by the following scheme:

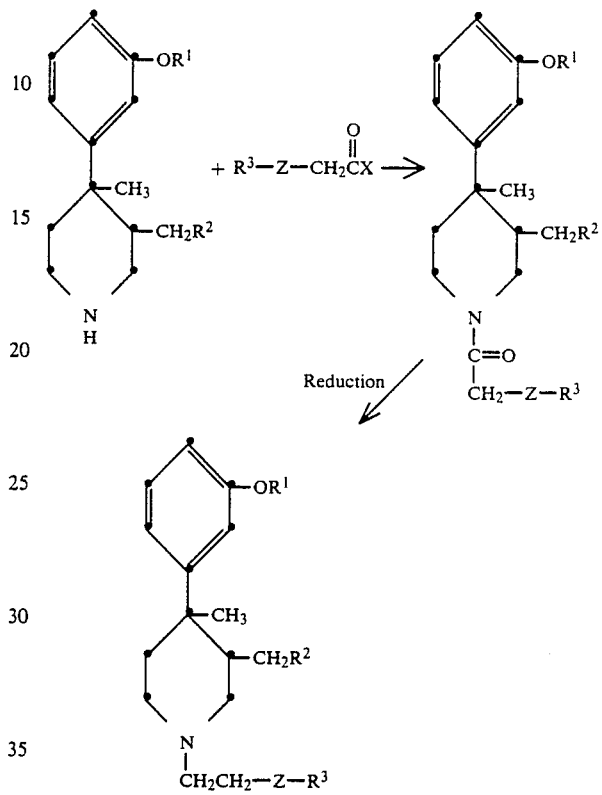

wherein $R^1$, $R^2$, $R^3$ and Z are as defined above and X is —OH, or a good leaving group such as

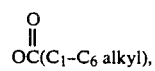

$C_1-C_6$ alkoxy or halogen.

The first step of the above-described process wherein X is hydroxy necessitates the use coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The direct coupling of a substituted carboxylic acid and a 3-substituted-4-methyl-4-(3-substitutedphenyl)piperidine is carried out by adding about an equimolar quantity of the piperidine starting material to a solution of the carboxylic acid in the presence of an equimolar quantity or slight excess of coupling reagent. The reaction generally is carried out in an unreactive organic solvent such as dichloromethane or N,N-dimethylformamide, and usually is complete within about twenty-four hours when conducted at a temperature of about 0° C. to about 30° C. The product is then typically isolated by filtration. The acylated product thus formed can be further purified, if needed, by any of several routine methods, including crystallization from common solvents, chromatography over solid supports such as silica or alumina, and related purification techniques.

The reaction wherein X is other than hydroxy is conducted as follows. The preferred leaving group in this reaction is where X is halogen, especially chloro. The reaction can be carried out by combining the substituted carboxylic acid derivative with about an equimolar quantity of the 3-substituted-4-methyl-4-(3-substituted phenyl)piperidine in a mutual solvent such tetrahydrofuran, diethyl ether, dichloromethane, dioxane, dimethylsulfoxide, N,N-dimethylformamide, benzene, toluene, and the like. If desired, a base can be utilized in the acylation reaction when X is halogen to act as an acid scavenger. Commonly used bases include sodium carbonate, potassium carbonate, pyridine, triethylamine and related bases. Bases such as pyridine act as their own solvent and need no additional solvent. The reaction generally is substantially complete after about two to about 200 hours when carried out at a temperature of about 20° C. to about 200° C., preferably from about 30° C. to about 100° C. The product of the reaction may be isolated by simply removing the reaction solvent, for instance by evaporation under reduced pressure. Also, the reaction mixture may be added to water, and the product collected by filtration or extracted into a water immiscible solvent. The product thus isolated can be further purified, if desired, by any of several well known techniques.

The acylated intermediates thus prepared are finally reduced according to standard procedures to provide the present compounds. Typical reducing agents suitable for use include the hydride reducing agents such as lithium aluminum hydride and sodium bis(2-methoxyethoxy)aluminum hydride, which is preferred. Typically, an excess of reducing agent is combined with the acylated intermediate in a mutual solvent. The reaction is substantially complete after about one to about 12 hours when conducted at a temperature in the range of about 20° C. to about 100° C. The desired product may then be isolated by procedures well known to those of ordinary skill in the art.

The compounds of the present invention may also be prepared by the direct substitution of a halogen substituted compound with the 3-substituted-4-methyl-4-(3-substituted phenyl)piperidine intermediate. This reaction is represented by the following scheme:

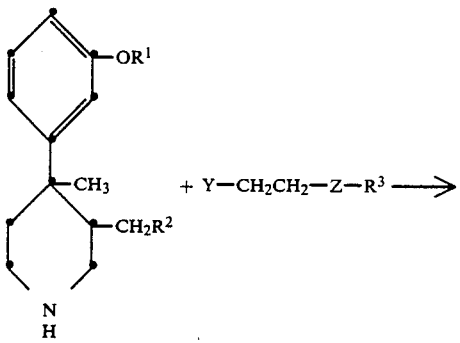

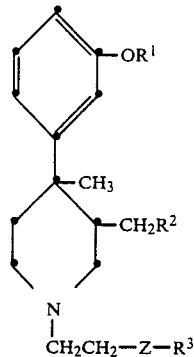

wherein $R^1$, $R^2$, $R^3$ and Z are as defined above and Y is halogen.

This reaction is conducted by combining approximately equimolar amounts of the two starting materials in a mutual solvent. A slight excess of the halogen substituted compound may be employed to ensure complete reaction. Typical mutual solvents suitable for use in this reaction include aprotic solvents such as N,N-dimethylformamide and the like. Further, the reaction is preferably conducted in the presence of a base, such as sodium bicarbonate, which acts as an acid scavenger for the hydrohalic acid which is formed as a by-product of the reaction. The reaction is generally complete after about 30 minutes to 24 hours when conducted at a temperature in the range of about 40° C. to about 100° C. The product is isolated and purified, if needed, by standard procedures. When $R^3$ is an alkene group in the above reaction, the double bond can be subsequently reduced under standard conditions to provide an alkyl substituent.

Compounds of the invention wherein Z is $$-\overset{\overset{O}{\|}}{C}-$$

may be prepared by the reaction of the 3-substituted-4-methyl-4-(3-substituted phenyl)piperidine starting material with an appropriately substituted keto substituted alkene. This reaction is represented by the following scheme:

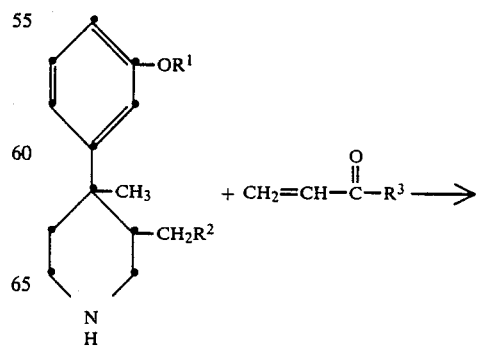

-continued

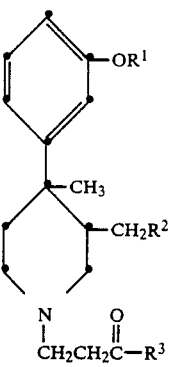

wherein R¹, R² and R³ are as defined above.

This reaction is conducted by combining approximately equimolar quantities of the starting materials in a mutual solvent such as N,N-dimethylformamide. The reaction is substantially complete after about 10 minutes to about 24 hours when conducted at a temperature in the range of about 20° C. to about 150° C. The product is isolated by standard procedures and purified, if desired, to provide a compound of the invention.

Compounds of the invention wherein Z is

and R⁴ is hydrogen are preferably prepared by reducing the corresponding compound wherein Z is

with a standard reducing agent such as any of the hydride reducing agents, for example lithium aluminum hydride, sodium borohydride and the like. This reaction is conducted in a non-reactive solvent, with any residual water preferable removed, such as tetrahydrofuran, diethyl ether, and related solvents. The product is isolated by standard procedures. When R⁴ is C₁–C₆ alkyl or benzyl, phenethyl, or phenpropyl, the alkali metal anion is formed with the R⁴=hydrogen compound, and reacted with the corresponding halide derivative. When R⁴ is acyl, the R⁴=hydrogen compound is acylated with an acyl halide, for example, according to standard acylation conditions.

Salts of piperidines are prepared by methods commonly employed for the preparation of amine salts. In particular, acid addition salts of the piperidines are prepared by reaction of the piperidine with an appropriate acid of pKa less than about 4, generally in an unreactive organic solvent. Suitable acids include mineral acids such as hydrochloric, hydrobromic, hydroiodic, sulfuric, phosphoric, and like acids. Organic acids are also used, for example acetic acid, p-toluenesulfonic acid, chloroacetic acid, and the like. The usual solvents used in the reaction include acetone, tetrahydrofuran, diethyl ether, ethyl acetate, and the like. Quaternary salts can be prepared in generally the same way by reaction of the piperidine with an alkylsulfate or alkyl halide, for example, methyl sulfate, methyl iodide, ethyl bromide, propyl iodide, and the like.

The 3-substituted-4-methyl-4-(3-hydroxy- or -alkanoyloxyphenyl)piperidine derivatives employed as starting materials in the synthesis of the compounds of the present invention are prepared by the general procedure taught by Zimmerman in U.S. Pat. No. 4,081,450, herein incorporated by reference. The compounds wherein R² is hydrogen are preferably prepared by the procedure of Barnett in U.S. Pat. No. 4,581,456, herein incorporated by reference, but adjusted so that β-stereochemistry is preferred, in contrast to the α-stereochemistry which is preferred by the process taught in the Barnett patent. According to the Barnett procedure, a 3-alkoxybromobenzene derivative is converted to the 3-alkoxyphenyllithium analog by reaction with an alkyllithium reagent. The 3-alkoxyphenyllithium derivative is reacted with a 1-alkyl-4-piperidone to provide the corresponding 1-alkyl-4-(3-alkoxyphenyl)-piperidinol derivative. The piperidinol thus prepared is dehydrated with acid to provide the corresponding 1-alkyl-4-(3-alkoxyphenyl)tetrahydropyridine derivative, which readily undergoes a metalloenamine alkylation to provide the appropriate 1-alkyl-4-methyl-4-(3-alkoxyphenyl)tetrahydropyridine derivative. The compound thus prepared is converted to a 1-alkyl-4-methyl-4-(3-alkoxyphenyl)-3-tetrahydropyridinemethanamine upon reaction with formaldehyde, an appropriate amine and sulfuric acid. Next, the methanamine is catalytically hydrogenated to the 1-alkyl-3,4-dimethyl-4-(3-alkoxyphenyl)piperidine, which is finally dealkylated at the 1-position, and the methoxy group is converted to a hydroxy group at the 3-position of the phenyl ring to provide the 3,4-dimethyl-4-(3-hydroxyphenyl)piperidine starting material employed in the present invention. This reaction sequence will be readily understood by the following scheme:

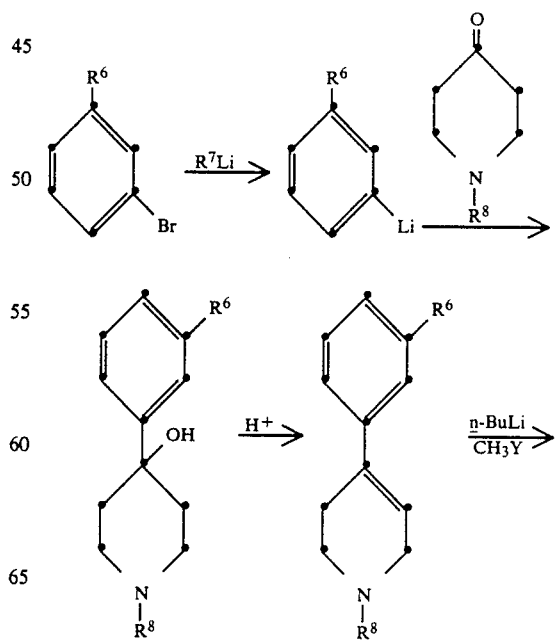

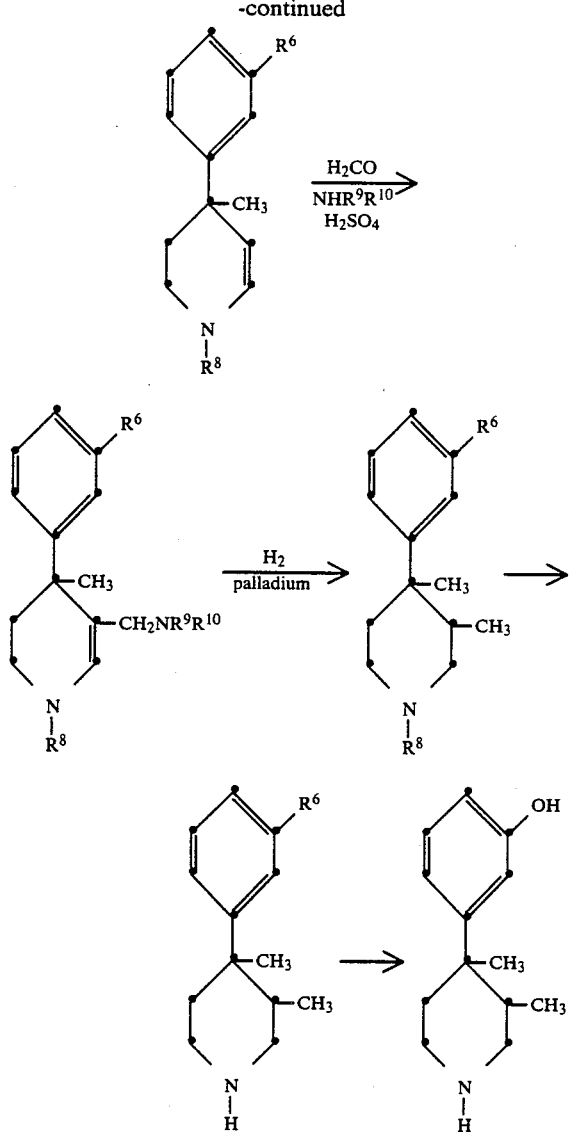

wherein $R^6$ is $C_1$–$C_3$ alkoxy, $R^7$ is $C_1$–$C_6$ alkyl, $R^8$ is $C_1$–$C_4$ alkyl, $R^9$ and $R^{10}$ independently are $C_1$–$C_3$ alkyl or, when taken together with the nitrogen atom to which they are attached, form piperidine, piperazine, N-methylpiperazine, morpholine or pyrrolidine, and Y is halogen.

The first step of the above-described process involves the formation of the 3-alkoxyphenyllithium reagent by reacting 3-alkoxybromobenzene with an alkyllithium reagent. This reaction is typically performed under inert conditions and in the presence of a suitable non-reactive solvent such as dry diethyl ether or preferably dry tetrahydrofuran. Preferred alkyllithium reagents used in this process are n-butyllithium, and especially sec.-butyllithium. Generally, approximately an equimolar to slight excess of alkyllithium reagent is added to the reaction mixture. The reaction is conducted at a temperature between about −20° C. and about −100° C., more preferably from about −50° C. to about −55° C.

Once the 3-alkoxyphenyllithium reagent has formed, approximately an equimolar quantity of a 1-alkyl-4-piperidone is added to the mixture while maintaining the temperature between −20° C. and −100° C. The reaction is typically complete after about 1 to 24 hours. At this point, the reaction mixture is allowed to gradually warm to room temperature. The product is isolated by the addition to the reaction mixture of a saturated sodium chloride solution in order to quench any residual lithium reagent. The organic layer is separated and further purified if desired to provide the appropriate 1-alkyl-4-(3-alkoxyphenyl)piperidinol derivative.

The dehydration of the 4-phenylpiperidinol prepared above is accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid and toluene or benzene. This reaction is typically conducted under reflux conditions, more generally from about 50° C. to about 150° C. The product thus formed is generally isolated by basifying an acidic aqueous solution of the salt form of the product and extracting the aqueous solution with any one of several water immiscible solvents. The resulting residue following evaporation may then be further purified if desired.

The 1-alkyl-4-methyl-4-(3-alkoxyphenyl)-tetrahydropyridine derivatives are prepared by a metalloenamine alkylation. This reaction is preferably conducted with n-butyllithium in tetrahydrofuran under an inert atmosphere, such as nitrogen or argon. Generally, a slight excess of n-butyllithium is added to a stirring solution of the 1-alkyl-4-(3-alkoxyphenyl)-tetrahydropyridine in THF cooled to a temperature in the range of from about −50° C. to about 0° C., more preferably from about −20° C. to about −10° C. This mixture is stirred for approximately 10 to 30 minutes followed by the addition of approximately from 1.0 to 1.5 equivalents of methyl halide to the solution while maintaining the temperature of the reaction mixture below 0° C. After about 5 to 60 minutes, water is added to the reaction mixture and the organic phase is collected. The product may be purified according to standard procedures, but it is desirable to purify the crude product by either distilling it under vacuum or slurrying it in a mixture of hexane:ethyl acetate (65:35, v:v) and silica gel for about two hours. According to the latter procedure, the product is then isolated by filtration and evaporating the filtrate under reduced pressure.

The next step in the process involves the application of the Mannich reaction of aminomethylation to non-conjugated, endocyclic enamines. This reaction is carried out by combining from about 1.2 to 2.0 equivalents of aqueous formaldehyde and about 1.3 to 2.0 equivalents of the secondary amine $NHR^9R^{10}$ in a suitable solvent. While water is the preferred solvent, other non-nucleophilic solvents such as acetone and acetonitrile may also be employed in this reaction. The pH of this solution is adjusted to approximately 3.0–4.0 with an acid which provides a non-nucleophilic anion. Examples of such acids include sulfuric acid, the sulfonic acids such as methanesulfonic acid and p-toluenesulfonic acid, phosphoric acid, and tetrafluoroboric acid. The preferred acid is sulfuric acid. To this solution is added one equivalent of a 1-alkyl-4-methyl-4-(3-alkoxyphenyl)tetrahydropyridine, typically dissolved in aqueous sulfuric acid, and the pH of the solution readjusted to from 3.0–3.5 with the non-nucleophilic acid or a secondary amine as defined above. While maintenance of this pH during the reaction is preferred for optimum results, this reaction may be conducted at a pH in the range of from about 1.0 to 5.0. The reaction is substantially complete after about 1 to 4 hours, more typically about 2 hours, when conducted at a temperature in the range of from about 50° C. to about 80° C., more preferably at about 70° C. The reaction is next cooled to approximately 30° C. and added to a sodium hydroxide solution. This solution is extracted with a water immiscible organic solvent, such as hexane or ethyl acetate, and the organic phase, following thorough washing with water to remove any residual formaldehyde, is evaporated to dryness under reduced pressure.

The next step of the process involves the catalytic hydrogenation of the 1-alkyl-4-methyl-4-(3-alkoxyphenyl)-3-tetrahydropyridinemethanamine prepared above to the corresponding trans 1-alkyl-3,4-dimethyl-4-(3-alkoxyphenyl)piperidine. This reaction actually occurs in two steps. The first step is the hydrogenolysis reaction wherein the exo C-N bond is reductively cleaved thereby generating the 3-methyltetrahydropyridine. In the second step, the 2,3-double bond in the tetrahydropyridine ring is reduced thereby affording the desired piperidine ring.

Reduction of the enamine double bond introduced the crucial relative stereochemistry at the 3 and 4 carbon atoms of the piperidine ring. The reduction does not occur with complete stereoselectivity. The catalysts employed in the process are chosen from among the various palladium and preferably platinum catalysts.

The catalytic hydrogenation step of the process is preferably conducted in an acidic reaction medium. Suitable solvents for use in the process include the alcohols, such as methanol or ethanol, as well as ethyl acetate, tetrahydrofuran, toluene, hexane, and the like.

Proper stereochemical outcome has been shown to be dependent on the quantity of catalyst employed. The quantity of catalyst required to produce the desired stereochemical result is dependent upon the purity of the starting materials in regard to the presence or absence of various catalyst poisons.

The hydrogen pressure in the reaction vessel is not critical but may be in the range of from about 5 to 200 psi. Concentration of the starting material by volume should preferably be around 20 ml. of liquid per gram of starting material, although an increased or decreased concentration of the starting material could also be employed. Under the conditions specified herein, the length of time for the catalytic hydrogenation is not critical because of the inability for over-reduction of the molecule. While the reaction may continue for up to 24 hours or longer, it is not necessary to continue the reduction conditions after the uptake of the theoretical two moles of hydrogen. The product is isolated by filtering the reaction mixture through infusorial earth and evaporating the filtrate to dryness under reduced pressure. Further purification of the product thus isolated is not necessary and preferably the diastereomeric mixture is carried directly on to the following reaction.

The alkyl substituent is next removed from the 1-position of the piperidine ring by standard dealkylation procedures. Preferably, a chloroformate derivative, especially the vinyl or phenyl derivatives, are employed and removed with acid. Next, the alkoxy compound prepared above is demethylated to the corresponding phenol. This reaction is generally carried out by reacting the compound in a 48% aqueous hydrobromic acid solution. This reaction is substantially complete after about 30 minutes to 24 hours when conducted at a temperature between 50° C. to about 150° C., more preferably at the reflux temperature of the reaction mixture. The mixture is then worked up by cooling the solution, followed by neutralization with base to an approximate pH of 8. This aqueous solution is extracted with a water immiscible organic solvent. The residue following evaporation of the organic phase is then preferably used directly in the following step.

The compounds employed as starting materials to the compounds of the invention may also be prepared by brominating the 1-alkyl-4-methyl-4-(3-alkoxyphenyl)-3-tetrahydropyridinemethanamine prepared above at the 3-position, lithiating the bromo intermediate thus prepared, and reacting the bromo intermediate with the halide $R^2CH_2Y$ to provide the corresponding 1-alkyl-3-substituted-4-methyl-4-(4-alkoxyphenyl)tetrahydropyridinemethanamine. This compound is then reduced and converted to the starting material as indicated above.

As noted above, the compounds of the present invention may exist as the resolved stereoisomers. The preferred procedure employed to prepare the resolved starting materials used in the synthesis of these compounds includes treating a 1,3-dialkyl-4-methyl-4-(3-alkoxyphenyl)piperidine with either (+)- or (−)-dibenzoyl tartaric acid to provide the resolved intermediate. This compound is dealkylated at the 1-position with vinyl chloroformate and finally converted to the desired 4-(3-hydroxyphenyl)piperidine isomer. This reaction is set forth in the following scheme:

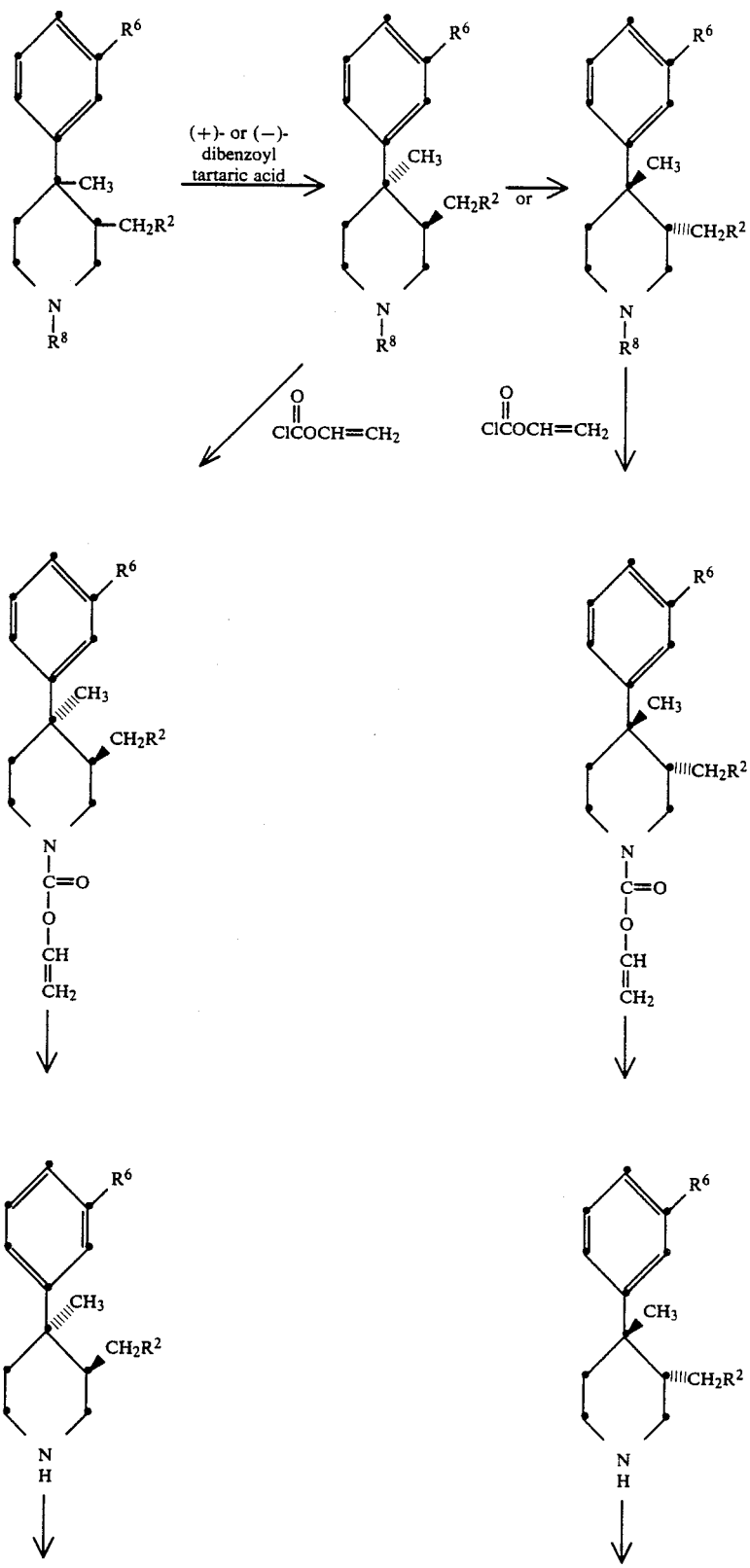

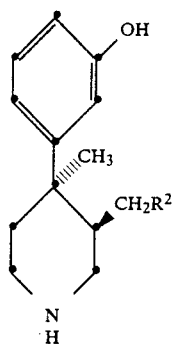

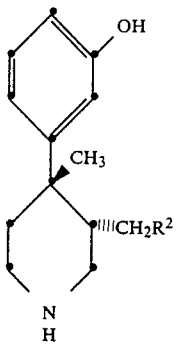

wherein $R^2$, $R^6$ and $R^8$ are as defined above.

As will be understood by those skilled in the art, the individual trans stereoisomers of the invention may also be isolated with either (+)- or (−)-dibenzoyl tartaric, as desired, from the corresponding racemic mixture of the trans isomer compounds of the invention.

The following Examples further illustrate certain of the compounds of the present invention, and methods for their preparation. The Examples are not intended to be limiting to the scope of the invention in any respect, and should not be so construed.

EXAMPLE 1 trans-(+)-1-(n-Hexyl)-3,4-dimethyl-4-(3-hydroxyphenyl)piperidine hydrochloride

A. trans-(+)-1-(n-Hexanoyl)-3,4-dimethyl-4-(3-hydroxyphenyl)piperidine

A 250 ml round bottom flask was charged with 2.0 g (9.76 mmol) of trans-(+)-3,4-dimethyl-4-(3-hydroxyphenyl)piperidine, 100 ml of N,N-dimethylformamide and 2.90 g (4 ml, 28.8 mmol) of triethylamine. To the mixture was added 3.94 g (29.63 mmol) of hexanoyl chloride. The reaction mixture was refluxed for approximately two hours and cooled to room temperature. The mixture was poured into 400 ml of water and extracted with diethyl ether three times. The ether extracts were combined and washed with 1N hydrochloric acid and a saturated sodium chloride solution. The organic phase was dried over anhydrous sodium sulfate and filtered. The filtrate was concentrated under vacuum and the resulting residue containing trans-(+)-1-(n-hexanoyl)-3,4-dimethyl-4-(3-hydroxyphenyl)piperidine was used directly in the following reaction.

B. A 250 ml round bottom flask was charged with 10 ml of Red-Al (sodium bis(2-methoxyethoxy)-aluminum hydride from Aldrich Chemical Company, Milwaukee, Wis.) and 20 ml of toluene. To the mixture was added dropwise a solution of the residue isolated above dissolved in approximately 50 ml of toluene. The reaction was stirred for approximately 60 minutes at room temperature and quenched by the addition of 400 ml of a pH 10 buffer. The pH of the mixture was adjusted to approximately 9.8 with 1N hydrochloric acid and the mixture was extracted with toluene. The organic extracts were combined and dried over anhydrous sodium sulfate. The filtrate was concentrated under vacuum and the resulting residue was chromatographed over silica gel while eluding with hexane:ethyl acetate (1.5:1, v:v). Fractions containing the major component were combined and the solvent was evaporated therefrom to provide the desired compound as the free base. The base was dissolved in diethyl ether and combined with hydrochloric acid to provide trans-(+)-1-(n-hexyl)-3,4-dimethyl-4-(3-hydroxyphenyl)piperidine hydrochloride.

Analysis calculated for $C_{19}H_{31}ClNO$ Theory: C, 70.02; H, 9.90; N, 4.30; Found: C, 70.27; H, 9.99; N, 4.48.

H—NMR (CDCl$_3$): δ7.30–6.62 (m, 4H); 2.91–1.40 (m, 11H); 1.32 (s, 6H); 1.29 (s, 3H); 0.88 (m, 3H); 0.76 (d, 3H, J=7 Hz)

Examples 2–7 were perpared by the general procedure set forth in Example 1.

EXAMPLE 2 trans-(−)-1-(n-Hexyl)-3,4-dimethyl-4-(3-hydroxyphenyl)piperidine hydrochloride

Analysis calculated for $C_{19}H_{31}ClNO$ Theory: C, 70.02; H, 9.90; N, 4.30; Found: C, 70.09; H, 9.81; N, 4.42.

H—NMR (CDCl$_3$): δ7.30–6.62 (m, 4H); 2.91–1.40 (m, 11H); 1.32 (s, 6H); 1.29 (s, 3H); 0.88 (m, 3H); 0.76 (d, 3H, J=7 Hz)

EXAMPLE 3 trans-(±)-1-(4-Methyl-4-pentenyl)-3,4-dimethyl-4-(3-hydroxyphenyl)piperidine hydrochloride, mp=95°–105° C.

Analysis calculated for $C_{19}H_{30}ClNO$ Theory: C, 70.45; H, 9.34; N, 4.32; Found: C, 70.52; H, 9.34; N, 4.23.

H—NMR (CDCl$_3$): δ0.76 (3H, d, J=7 Hz); 1.3 (3H, s); 1.72 (3H, s); 4.7 (2H, d, J=5 Hz); 6.64 (1H, dd); 6.77 (1H, s); 6.86 (1H, d, J=7 Hz); 7.18 (1H, t, J=6 Hz)

EXAMPLE 4 trans-(±)-1-(5-Methylhexyl)-3,4-dimethyl-4-(3-hydroxyphenyl)piperidine hydrochloride, mp=175°–177° C.

Analysis calculated for $C_{20}H_{36}ClNO$ Theory: C, 70.66; H, 10.08; N, 4.12; Found: C, 71.00; H, 9.84; N, 4.44.

H—NMR (CDCl$_3$): δ7.30–6.60, (m, 4H); 3.66–1.12 (m, 20H); [1.10 (d, J=7H2), 0.97 (d, J=7H2), 3H]; 0.90–0.76 (m, 5H)

EXAMPLE 5 trans-(±)-1-(Cyclopentylmethyl)-3,4-dimethyl-4-(3-hydroxyphenyl)piperidine hydrochloride Analysis calculated for $C_{19}H_{31}ClNO$ Theory: C, 70.45; H, 9.34; N, 4.32; Found: C, 70.68; H, 9.14; N, 4.58.

H—NMR (CDCl$_3$): δ7.31–6.64 (m, 4H); 3.70–1.42 (m, 18H); [1.40 (s), 1.36 (s), 3H]; [1.10 (d, J=8 Hz), 1.00 (d, J=8 Hz), 3H] ppm

EXAMPLE 6 trans-(±)-1-(2-Cyclopentylethyl)-3,4-dimethyl-4-(3-hydroxyphenyl)piperidine hydrochloride H—NMR (CDCl$_3$): δ0.76 (3H, d, J=7 Hz) 1.32 (3H, s); 2.8–2.9 (1H, m); 6.65 (1H, m); 6.75 (1H, s); 6.85 (1H, d, J=8 Hz); 7.15 (1H, t, J=6 Hz)

EXAMPLE 7 trans-(±)-1-[2-(2-Cyclopenten-1-yl)ethyl]-3,4-dimethyl-4-(3-hydroxyphenyl)piperidine hydrochloride, mp=100°–130° C.

Analysis calculated for C$_{20}$H$_{30}$ClNO Theory: C, 71.51; H, 9.00; N, 4.17; Found: C, 71.25; H, 8.92; N, 4.29.
H—NMR (CDCl$_3$): δ0.75 (3H, d, J=6 Hz); 1.32 (3H, s); 5.72 (2H, m); 6.65 (1H, d, J=7 Hz); 6.75 (1H, s); 6.85 (1H, d, J=6 Hz); 7.16 (1H, t, J=7 Hz)

EXAMPLE 8 trans-(±)-1-(n-Heptyl)-3,4-dimethyl-4-(3-hydroxyphenyl)piperidine hydrochloride

To a solution of 1.0 g (0.0049 mol) of trans-(±)-3,4-dimethyl-4-(3-hydroxyphenyl)piperidine and 1.25 g (0.012 mol) of triethylamine in 20 ml of N,N-dimethylformamide was added 1.8 g (0.012 mol) of heptanoyl chloride. The reaction mixture was stirred at room temperature for approximately one hour and poured into 200 ml of water. The resulting mixture was extracted five times with 100 ml portions of ethyl acetate, and the organic phases were combined. The organic solution was washed with 200 ml of 1N hydrochloric acid, 200 ml of a saturated sodium bicarbonate solution, and 200 ml of brine, and dried over a mixture of sodium chloride and anhydrous sodium sulfate. The dried organic solution was concentrated under vacuum and the residue was dissolved in diethyl ether. This solution was cooled to approximately 0° C. and 600 mg (0.016 mol) of lithium aluminum hydride was added. The mixture was stirred at room temperature for one hour and 0.6 ml of water was added, followed by the addition of 1.8 ml of 15% sodium hydroxide and 0.6 ml of water. The solution was filtered and the filtrate was dried over sodium chloride and anhydrous sodium sulfate. The organic phase was evaporated under vacuum and the residue was chromatographed over silica gel employing hexane:ethyl acetate (3:1, v:v) containing 0.5% by volume of triethylamine as the eluent. Fractions containing the major component were combined and the solvent was evaporated therefrom. The hydrochloride salt was prepared to provide the title compound. mp=155°–157° C.

Analysis calculated for C$_{20}$H$_{34}$ClNO Theory: C, 70.66; H, 10.08; N, 4.12; Found: C, 70.83; H, 9.79; N, 3.89.

H—NMR (CDCl$_3$): δ7.28–6.48 (m, 4H); 1.28 (s, 3H); 0.85 (m, 3H); 0.75 (d, 3H, J=7 Hz)

Examples 9–12 were prepared by the general procedure set forth in Example 8.

EXAMPLE 9 trans-(±)-1-(3-Cyclopentylpropyl)-3,4-dimethyl-4-(3-hydroxyphenyl)piperidine hydrochloride, mp=171°–174° C.

Analysis calculated for C$_{21}$H$_{24}$ClNO Theory: C, 71.66; H, 9.74; N, 3.98; Found: C, 71.53; H, 9.46; N, 4.06.
H—NMR (CDCl$_3$): δ7.19–6.48 (m, 4H); 3.60 (t, 2H, J=7 Hz); 1.25 (s, 3H); 0.78 (d, 3H, J=7 Hz)

EXAMPLE 10 trans-(±)-1-(Cyclohexylmethyl)-3,4-dimethyl-4-(3-hydroxyphenyl)piperidine hydrochloride, mp=80° C.

Analysis calculated for C$_{20}$H$_{32}$ClNO Theory: C, 71.08; H, 9.55; N, 4.14; Found: C, 70.85; H, 9.48; N, 3.78.
H—NMR (CDCl$_3$): δ7.20–6.49 (m, 4H); 3.44 (d, 2H, J=7 Hz); 1.28 (s, 3H); 0.76 (d, 3H, J=7 Hz)

EXAMPLE 11 trans-(±)-1-(3-Cyclohexylpropyl)-3,4-dimethyl-4-(3-hydroxyphenyl)piperidine hydrochloride, mp=195°–197° C.

Analysis calculated for C$_{22}$H$_{36}$ClNO Theory: C, 72.20; H, 9.92; N, 3.83; Found: C, 71.98; H, 9.79; N, 3.85.
H—NMR (CDCl$_3$): δ7.19–6.48 (m, 4H); 3.60 (t, 2H, J=7 Hz); 1.28 (s, 3H); 0.75 (d, 3H, J=7 Hz)

EXAMPLE 12 trans-(±)-1-(3,3-Dimethylbutyl)-3,4-dimethyl-4-(3-hydroxyphenyl)piperidine hydrochloride, mp=198°–200° C.

Analysis calculated for C$_{19}$H$_{32}$ClNO Theory: C, 70.02; H, 9.90; N, 4.30; Found: C, 70.19; H, 9.66; N, 4.38.
H—NMR (CDCl$_3$): δ7.22–6.59 (m, 4H); 3.70–1.66 (m, 11H); 1.59 (s, 3H); [1.42 (s), 1.37 (s) 3H]; [1.16 (d, J=7H2), 1.02 (d, J=7H2) 3H]; 0.99 (s, 3H); 0.91 (s, 3H)

EXAMPLE 13 trans-(±)-1-(2-Cyclohexylethyl)-3,4-dimethyl-4-(3-hydroxyphenyl)piperidine hydrochloride To a solution of 500 mg (2.4 mmol) of trans-(±)-3,4-dimethyl-4-(3-hydroxyphenyl)piperidine dissolved in 50 ml of N,N-dimethylformamide was added 244 mg (2.9 mmol) of sodium bicarbonate and 554 mg (2.9 mmol) of 2-cyclohexylethylbromide. The reaction mixture was refluxed for one hour and cooled to room temperature. The mixture was poured into ice and the pH was adjusted to about 9.8. The mixture was extracted with diethyl ether and the organic phases were combined and dried over anhydrous potassium carbonate. The solvent was evaporated under vacuum to provide 690 ml of crude material. The hydrochloride salt was prepared to provide a total of 330 mg of cis-(±)-1-(2-cyclohexyl-ethyl)-3,4-dimethyl-4-(3-hydroxyphenyl)-piperidine hydrochloride. mp=178°–180° C.

Analysis calculated for C$_{21}$H$_{34}$ClNO Theory: C, 71.66; H, 9.74; N, 3.98; Found: C, 71.36; H, 9.93; N, 4.23.
H—NMR (CDCl$_3$): δ0.77 (3H, d, J=6 Hz); 1.32 (3H, s); 1.48–1.78 (10H, m); 6.64 (1H, dd); 6.78 (1H, s); 6.87 (1H, d, J=6 Hz); 7.18 (1H, t, J=6 Hz)

Examples 14–16 were prepared by the general procedure outlined in Example 13.

EXAMPLE 14 trans-(±)-1-(n-Pentyl)-3,4-dimethyl-4-(3-hydroxyphenyl)piperidine hydrochloride

Analysis calculated for C$_{18}$H$_{30}$ClNO Theory: C, 69.32; H, 9.70; N, 4.49; Found: C, 69.43; H, 9.85; N, 4.67.
H—NMR (CDCl$_3$): δ0.75 (3H, d, J=6 Hz); 0.88 (3H, t, J=6 Hz); 1.3 (3H, s); 1.98 (1H, m); 6.64 (1H, dd); 6.75 (1H, s); 6.83 (1H, d, J=7 Hz); 7.15 (1H, t, J=9 Hz)

EXAMPLE 15 trans-(±)-1-(4-Methylpentyl)-3,4-dimethyl-4-(3-hydroxyphenyl)piperidine hydrochloride Analysis calculated for $C_{19}H_{32}ClNO$ Theory: C, 70.02; H, 9.90; N, 4.30; Found: C, 69.89; H, 9.77; N, 4.27.
H—NMR (CDCl$_3$): δ0.77 (3H, d, J=7 Hz); 0.88 (6H, d, J=7 Hz); 1.32 (3H, s); 6.62 (1H, dd); 6.76 (1H, s); 6.83 (1H, d, J=6 Hz); 7.15 (1H, t, J=6 Hz)

EXAMPLE 16 trans-(±)-1-(3-Methylbutyl)-3,4-dimethyl-4-(3-hydroxyphenyl)piperidine hydrochloride, mp=155°–158° C.

Analysis calculated for $C_{18}H_{30}ClNO$ Theory: C, 69.32; H, 9.70; N, 4.49; Found: C, 69.50; H, 9.66; N, 4.45.
H—NMR (CDCl$_3$): δ0.77 (3H, d, J=6 Hz); 0.89 (6H, d, J=6 Hz); 6.62 (1H, dd); 6.78 (1H; s); 6.87 (1H, d, J=6 Hz); 7.15 (1H, t, J=7 Hz)

EXAMPLE 17 trans-(±)-1-(1-Cyclopentylpropanon-3-yl)-3,4-dimethyl-4-(3-hydroxyphenyl)piperidine hydrochloride, mp=80°–100° C.

To a solution of 1.0 g of trans-(±)-3,4-dimethyl-4-(3-hydroxyphenyl)piperidine in 60 ml of N,N-dimethylformamide was added to 5.0 g of 3-cyclopentylpropen-3-one. The mixture was stirred at room temperature for 3 hours and poured into a mixture of diethylether and water. The mixture was washed with a saturated sodium chloride solution and the organic phase was separated, dried over anhydrous potassium carbonate and concentrated under vacuum to provide 1.8 g of the free base. This material was purified over a silicone dioxide resin and converted to the hydrochloride salt to provide the desired compound. The elemental analysis was calculated for the free base.

Analysis calculated for $C_{21}H_{31}NO_2$ Theory: C, 76.55; H, 9.48; N, 4.25; Found: C, 76.28; H, 9.59; N, 4.12.
H—NMR (CDCl$_3$): δ0.74 (3H, d, J=7 Hz); 1.30 (3H, s); 6.63 (1H, d, J=8 Hz); 6.74 (1H, s); 6.84 (1H, d, J=6 Hz); 7.16 (1H, t, J=6 Hz)

EXAMPLE 18 trans-(±)-1-[R,S-(1-Cyclopentylpropanol-3-yl)]-3,4-dimethyl-4-(3-hydroxyphenyl)piperidine hydrochloride To a solution of trans-(±)-1-(1-cyclopentylpropanon-3-yl)-3,4-dimethyl-4-(3-hydroxyphenyl)piperidine in 100 ml of dry diethyl ether was added 2.0 ml of 1M lithium aluminum hydride in THF. The mixture was refluxed for 90 minutes and cooled to about 0° C. Five milliliters of ethyl acetate were added to the mixture followed by sufficient water to result in a crystallization. The solid was decanted and the resulting filtrate was dried over anhydrous potassium carbonate. The filtrate was concentrated under vacuum and converted to the hydrochloride salt to provide the desired compound. The elemental analysis was calculated for the free base.

Analysis calculated for $C_{21}H_{33}NO_2$ Theory: C, 76.09; H, 10.03; N, 4.23; Found: C, 76.07; H, 10.09; N, 4.01.
H—NMR (CDCl$_3$): δ0.54 (3H, d, J=6 Hz); 1.28 (3H, s); 3.62 (1H, q, J=10 Hz); 6.6 (1H, d, J=8 Hz); 6.71 (2H, t, J=9 Hz); 7.1 (1H, t, J=9 Hz); 7.47 (1H, broad singlet).

Examples 19–34 were prepared by the general procedures outlined above.

EXAMPLE 19 trans-(±)-1-(3-Oxo-4-methylpentyl)-3,4-dimethyl-4-(3-hydroxyphenyl)piperidine hydrochloride Analysis calculated for $C_{19}H_{30}ClNO_2$ Theory: C, 67.14; H, 8.90; N, 4.12; Found: C, 67.43; H, 8.83; N, 3.82.

EXAMPLE 20 trans-(±)-1-[R,S-(3-Hydroxy-4-methylpentyl)]-3,4-dimethyl-4-(3-hydroxyphenyl)piperidine hydrochloride Analysis calculated for $C_{19}H_{32}ClNO_2$ Theory: C, 66.74; H, 9.43; N, 4.10; Found: C, 66.54; H, 9.45; N, 4.30.
H—NMR (CDCl$_3$): δ0.6 (3H, t, J=6 Hz); 0.92 (3H, t, J=4 Hz); 0.98 (3H, t, J=5 Hz); 1.3 (3H, s); 6.62 (1H, d, J=8 Hz); 6.74 (2H, m); 7.12 (1H, t, J=6 Hz); 7.4–7.2 (1H, broad singlet)

EXAMPLE 21 trans-(±)-1-(5-n-Hexenyl)-3,4-dimethyl-4-(3-hydroxyphenyl)piperidine hydrochloride Analysis calculated for $C_{19}H_{30}ClNO$ Theory: C, 70.45; H, 9.34; N, 4.32; Found: C, 70.68; H, 9.13; N, 4.16.
H—NMR (CDCl$_3$): δ0.77 (3H, d, J=6 Hz); 1.3 (3H, s); 4.92–5.06 (2H, m); 5.74–5.9 (1H, m); 6.64 (1H, m); 6.76 (1H, s); 6.85 (1H, d, J=7 Hz); 7.16 (1H, t, J=7 Hz)

EXAMPLE 22 trans-(±)-1-(n-Hexyl)-3,4-dimethyl-4-(3-hydroxyphenyl)piperidine hydrochloride

Analysis calculated for $C_{19}H_{32}ClNO$ Theory: C, 70.02; H, 9.90; N, 4.30; Found: C, 69.79; H, 10.15; N, 4.17.
H—NMR (CDCl$_3$): δ0.76 (3H, d, J=6 Hz); 0.82–0.92 (3H, broad triplet); 1.3 (3H, s); 6.63 (1H, m); 6.75 (1H, s); 6.85 (1H, d, J=7 Hz); 7.17 (1H, t, J=7 Hz).

EXAMPLE 23 trans-(+)-1-[S-(3-Hydroxy-3-cyclohexylpropyl)]-3,4-dimethyl-4-(3-hydroxyphenyl)piperidine, mp=142°–143° C.

Analysis calculated for $C_{22}H_{35}NO_2$ Theory: C, 76.48; H, 10.21; N, 4.05; Found: C, 76.64; H, 10.48; N, 4.17.

EXAMPLE 24 trans-(−)-1-[S-(3-Hydroxy-3-cyclohexylpropyl)]-3,4-dimethyl-4-(3-hydroxyphenyl)piperidine, mp=151°–152° C.

$[α]_{589} = -64.9655$, $[α]_{365} = -211.655$
Analysis calculated for $C_{22}H_{35}NO_2$ Theory: C, 76.48; H, 10.21; N, 4.05; Found: C, 76.71; H, 10.43; N, 4.05.

EXAMPLE 25 trans-(+)-1-[R-(3-Hydroxy-3-cyclohexylpropyl)]-3,4-dimethyl-4-(3-hydroxyphenyl)piperidine, mp=150°–151° C.

$[α]_{589} = +73.6069$, $[α]_{365} = +238.963$
Analysis calculated for $C_{22}H_{35}NO_2$ Theory: C, 76.48; H, 10.21; N, 4.05; Found: C, 76.24; H, 9.92; N, 4.18.

EXAMPLE 26 trans-(−)-1-[R-(3-Hydroxy-3-cyclohexylpropyl)]-3,4-dimethyl-4-(3-hydroxyphenyl)piperidine, mp=141°–143° C.

$[α]_{589} = -68.81$, $[α]_{365} = -223.88$,

Analysis calculated for $C_{22}H_{35}NO_2$ Theory: C, 76.48; H, 10.21; N, 4.05; Found: C, 76.40; H, 10.35; N, 4.01.

EXAMPLE 27 trans-($\pm$)-1-[R,S-(3-Hydroxy-3-cyclohexylpropyl)]-3,4-dimethyl-4-(3-hydroxyphenyl)piperidine hydrochloride Analysis calculated for $C_{22}H_{36}ClNO_2$ Theory: C, 69.18; H, 9.50; N, 3.67; Found: C, 68.97; H, 9.37; N, 3.70.

EXAMPLE 28 trans-(+)-1-(5-Methylhexyl)-3,4-dimethyl-4-(3-hydroxyphenyl)piperidine hydrochloride $[\alpha]_{365} = +195.429$ Analysis calculated for $C_{20}H_{34}ClNO$ Theory: C, 70.66; H, 10.08; N, 4.12; Found: C, 70.42; H, 9.95; N, 4.09.

EXAMPLE 29 trans-(−)-1-(5-Methylhexyl)-3,4-dimethyl-4-(3-hydroxyphenyl)piperidine hydrochloride $[\alpha]_{365} = -207.669$ Analysis calculated for $C_{20}H_{34}ClNO$ Theory: C, 70.66; H, 10.08; N, 4.12; Found: C, 70.40; H, 10.31; N, 4.32.

EXAMPLE 30 trans-($\pm$)-1-[R,S-(3-Hydroxyhexyl)]-3,4-dimethyl-4-(3-hydroxyphenyl)piperidine hydrochloride Analysis calculated for $C_{19}H_{32}ClNO_2$ Theory: C, 66.74; H, 9.43; N, 4.10; Found: C, 66.90; H, 9.20; N, 4.19.

EXAMPLE 31 trans-($\pm$)-1-[R,S-(3-Methoxy-3-cyclohexylpropyl)]-3,4-dimethyl-4-(3-hydroxyphenyl)piperidine hydrochloride, mp=171°–173° C.

Analysis calculated for $C_{23}H_{38}ClNO_2$ Theory: C, 69.76; H, 9.67; N, 3.54; Found: C, 70.00; H, 9.93; N, 3.45.

EXAMPLE 32 trans-($\pm$)-1-(3-Oxo-n-octyl)-3,4-dimethyl-4-(3-hydroxyphenyl)piperidine hydrochloride, mp=122°–123° C.

Analysis calculated for $C_{21}H_{34}ClNO_2$ Theory: C, 68.55; H, 9.31; N, 3.81; Found: C, 68.82; H, 9.51; N, 3.71.

EXAMPLE 33 trans-($\pm$)-1-(3-Oxo-3-cyclohexylpropyl)-3,4-dimethyl-4-(3-hydroxyphenyl)piperidine hydrochloride, mp=170°–173° C.

Analysis calculated for $C_{22}H_{35}ClNO_2$ Theory: C, 69.54; H, 9.02; N, 3.69; Found: C, 69.39; H, 8.84; N, 3.85.

EXAMPLE 34 trans-($\pm$)-1-(3-Oxo-n-hexyl)-3,4-dimethyl-4-(3-hydroxyphenyl)piperidine hydrochloride Analysis calculated for $C_{19}H_{30}ClNO_2$ Theory: C, 69.14; H, 8.96; N, 4.12; Found: C, 69.36; H, 8.85; N, 4.34.

EXAMPLE 35 trans-($\pm$)-1-[3-(2-Thienyl)propyl]-3,4-dimethyl-4-(3-hydroxyphenyl)piperidine hydrochloride A. 3-(2-Thienyl)propionyl chloride To a solution of 5.0 g (0.032 mol) of 3-(2-thienyl)propionic acid in 2 ml of methylene chloride and 25 ml of oxalyl chloride was added three drops of N,N-dimethylformamide slowly. Following evolution of the gas the reaction mixture was concentrated under vacuum and 20 ml of hexane was added to the residue. The resulting mixture was filtered and the filtrate was concentrated under vacuum. The resulting compound, 3-(2-thienyl)propionyl chloride, was used directly in the following reaction.

B. To a solution of 1.0 g (4.9 mmol) of trans-($\pm$)-3,4-dimethyl-4-(3-hydroxyphenyl)piperidine and 2.6 g of 1,8-bis(dimethylamino)naphthalene dissolved in 30 ml of N,N-dimethylformamide was added a solution of 2.2 g (0.0126 mol) of 3-(2-thienyl)propionyl chloride dissolved in 20 ml of N,N-dimethylformamide dropwise. The reaction mixture was stirred at room temperature for approximately one hour and poured into 250 ml of water. The mixture was extracted with five 100 ml portions of ethyl acetate. The organic extracts were combined, washed with 1N hydrochloric acid, an aqueous saturated sodium bicarbonate solution, and a saturated sodium chloride solution and dried over a mixture of sodium chloride and anhydrous sodium sulfate. The organic phase was evaporated under vacuum and the residue was dissolved in 200 ml of toluene. This mixture was evaporated and the residue was dissolved in 50 ml of tetrahydrofuran. The mixture was cooled to about 0° C., a solution of 5 ml of Red-Al (3.4M solution of sodium bis(2-methoxyethoxy)aluminum hydride in toluene from Aldrich Chemical Company, Milwaukee, Wis.) in 50 ml of tetrahydrofuran was added. The resulting mixture was stirred at room temperature for approximately one hour and 100 ml of pH 10 buffer was added. This solution was extracted with two 100 ml portions of ethyl acetate. The organic extracts were combined, washed with an aqueous saturated sodium chloride solution and dried over sodium chloride and anhydrous sodium sulfate. The organic solution was evaporated under vacuum and the residue was dissolved in 50 ml of ethyl acetate. The mixture was extracted with two 100 ml portions of 1N hydrochloric acid and the acidic extracts were combined and washed with diethyl ether. The pH of the aqueous mixture was adjusted to about 9.8 with sodium hydroxide, and the aqueous mixture was extracted twice with a total of 200 ml ethyl acetate. The extracts were combined and washed with an aqueous saturated sodium chloride solution, dried over sodium chloride and anhydrous sodium sulfate and concentrated under vacuum. The resulting residue was chromatographed employing hexane:ethyl acetate (3:1, v:v) containing 0.5% triethylamine by volume as the eluant. The hydrochloride salt was prepared to provide the title compound. mp=101°–103° C.

Analysis calculated for $C_{20}H_{28}ClNOS$ Theory: C, 65.64; H, 7.71; N, 3.83; Found: C, 65.37; H, 7.98; N, 4.02.

H—NMR (CDCl$_3$): $\delta$7.21–6.50 (m, 7H); 1.27 (s, 3H); 0.77 (d, 3H, J=7 Hz)

Following the general procedures set forth above the remaining Examples were prepared.

EXAMPLE 36 trans-(+)-1-[3-(2-Thienyl)propyl]-3,4-dimethyl-4-(3-hydroxyphenyl)piperidine, mp=110°–112° C.

Analysis calculated for $C_{20}H_{28}ClNOS$ Theory: C, 65.64; H, 7.71; N, 3.83; Found: C, 65.40; H, 7.49; N, 3.77.

H—NMR (CDCl$_3$): $\delta$7.4–6.54 (m, 7H); 3.46–1.7 (m, 13H); 1.34 (s, 3H); 0.76 (d, 3H, J=7 Hz)

EXAMPLE 37 trans-(—)-1-[3-(2-Thienyl)propyl]-3,4-dimethyl-4-(3-hydroxyphenyl)piperidine hydrochloride $M^+ = 329$ Analysis calculated for $C_{20}H_{28}ClNOS$ Theory: C, 65.64; H, 7.71; N, 3.83; Found: C, 65.94; H, 7.49; N, 3.95.
H—NMR (CDCl$_3$): δ7.4–6.54 (m, 7H); 3.46–1.7 (m, 13H); 1.34 (s, 3H); 0.76 (d, 3H, J=7 Hz)

EXAMPLE 38 trans-(±)-1-[2-(2-Thienyl)ethyl]-3,4-dimethyl-4-(3-hydroxyphenyl)piperidine hydrochloride, mp=117°–119° C.

Analysis calculated for $C_{19}H_{26}ClNOS$ Theory: C, 64.84; H, 7.45; N, 3.98; Found: C, 65.09; H, 7.62; N, 3.69.

EXAMPLE 39 trans-(±)-1-[3-Oxo-3-(2-thienyl)propyl]-3,4-dimethyl-4-(3-hydroxyphenyl)piperidine hydrochloride, mp=118°–120° C.

Analysis calculated for $C_{20}H_{26}ClNO_2S$ Theory: C, 63.22; H, 6.70; N, 3.67; Found: C, 62.78; H, 6.31; N, 3.68.

EXAMPLE 40 trans-(±)-1-[R,S-[3-Hydroxy-3-(2-thienyl)-propyl]-3,4-dimethyl-4-(3-hydroxyphenyl)piperidine hydrochloride, mp=97°–99° C.

Analysis calculated for $C_{20}H_{28}ClNO_2S$ Theory: C, 62.89; H, 7.39; N, 3.67; Found: C, 62.79; H, 7.36; N, 3.73.

EXAMPLE 41 trans-(±)-1-[3-(3-Thienyl)propyl]-3,4-dimethyl-4-(3-hydroxyphenyl)piperidine hydrochloride Analysis calculated for $C_{20}H_{28}ClNOS$ Theory: C, 65.64; H, 7.71; N, 3.83; Found: C, 65.42; H, 7.52; N, 3.92.

As noted above, the compounds of the present invention are useful in blocking the effect of agonists at mu or kappa receptors. As such, the present invention also provides a method for blocking mu or kappa receptors in mammals comprising administering to a mammal requiring blocking of a mu or kappa receptor a receptor blocking dose of a compound of the invention.

The term "receptor blocking dose", as defined herein, means an amount of compound necessary to block a mu or kappa receptor following administration to a mammal requiring blocking of a mu or kappa receptor. The active compounds are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to influence by mu and kappa receptors in the brain. As such, the compounds of the present invention are believed to have the ability to treat a variety of disorders in mammals associated with these receptors such as eating disorders, opiate overdose, depression, smoking, alcoholism sexual dysfunction, shock, stroke, spinal damage and head trauma. As such, the present invention also provides methods of treating the above disorders at rates set forth above for blocking the effect of agonists at mu or kappa receptors.

The compounds of the present invention have been found to display excellent activity in an opioid receptor binding assay which measures the ability of the compounds to block the mu or kappa receptors. This assay was conducted by the following procedure.

Male Sprague Dawley rats for mu and delta site experiments and male Hartley guinea pigs for kappa site experiments were sacrificed via decapitation and the brains were removed. The brain tissue, rat whole brain minus cerebellum for mu and delta sites and guinea pig cortex for the kappa site, was homogenized in a Teflon and glass tissue homogenizer. A supernatant I, pellet IV, fraction was frozen in a nitrogen freezer at 1.33 g/ml concentration and stored for not longer than five weeks prior to use. Pellets were rehydrated with physiological buffer prior to use.

For mu and delta sites increasing concentrations of experimental compound, (0.1 to 1000 nanomolar (nM)), Kreb-Hepes buffer pH 7.4, and $^3$H ligand were combined in polystyrene tubes at room temperature. The reaction was initiated by the addition of the rehydrated tissue which has been preincubated at 37° C. for 20 minutes. The reaction mixture was incubated in a 37° C. water bath for 20 minutes. The reaction was terminated by rapid filtration, (Amicon vacuum manifolds), through Whatman GF/C glass filters that had been presoaked in Krebs-Hepes buffer pH 7.4. The filters were then washed 2× with 5 ml of ice cold Krebs-Hepes buffer pH 7.4. Washed filters were placed in scintillation vials and 10 ml PCS, (Amersham), was added and samples counted in a Searle D-300 beta counter. Means and standard error statistics were calculated for triplicate experimental determinations in certain cases. The procedure was slightly modified for the kappa site. The tissue was pretreated with 100 nM concentrations of mu and delta receptor site blockers. The incubation time for the reaction mixture was 45 minutes at 37° C.

Ki values were calculated using a minitab statistical program according to the following formula:

$$K_i = \frac{IC_{50}}{1 + \frac{\text{concentration of }^3\text{H ligand}}{K_D}}$$

wherein $IC_{50}$ is the concentration at which 50% of the $^3$H ligand is displaced by the test compound and $K_D$ is the dissociation constant for the $^3$H ligand at the receptor site.

The results of the evaluation of certain compounds of the present invention in the opioid receptor binding assay are set forth below in Table I. In the Table, column 1 sets forth the Example Number of the compound evaluated; column 2, the Ki value in nanomolar (nM) at the mu receptor; and column 3, the Ki value in nM at the kappa receptor. Also in the Table, compounds identified as Compounds A-F in Tables I-IV which follow are known compounds which were evaluated to compare their activity to the compounds of the present invention. Compounds A-F have the following identities:

Compound A: 4β-(3-Hydroxyphenyl)-3β,4α-dimethyl-α-phenyl-1-piperidinepropanol hydrochloride Compound B: 3-(1,3α,4β-Trimethyl-4α-piperidyl)-phenol hydrochloride Compound C: 3-[4β-(3-Hydroxyphenyl)-3β,4α-dimethylpiperidino]propiophenone maleate Compound D: 3-(3α,4β-Dimethyl-1-phenethyl-4α-piperidyl)phenol hydrochloride Compound E: naloxone Compound F: naltrexone

TABLE I

Opioid Receptor Binding Displacement Assay

| Example No. of Compound Tested | Ki Mu (nM) | Ki Kappa (nM) |
|---|---|---|
| 1 | 1.10 | 5.20 |
| 2 | 5.61 | 5.79 |
| 3 | 2.95 ± 1.12 | 13.89 ± 6.66 |
| 4 | 0.46 ± 0.20 | 6.04 ± 0.44 |
| 6 | 0.94 | 7.18 |
| 7 | 12.06 | 1.04 |
| 8 | 0.62 | — |
| 9 | 0.37 ± 0.07 | 3.41 ± 0.08 |
| 10 | 17.10 | 28.2 |
| 11 | 0.49 | 2.34 |
| 13 | 0.65 ± 0.12 | 2.32 ± 0.26 |
| 14 | 4.33 | — |
| 15 | 1.25 ± 0.40 | 9.43 ± 1.67 |
| 16 | 31.75 | 70.10 |
| 17 | 0.84 | 0.55 |
| 18 | 0.41 | 5.47 |
| 21 | 1.61 | — |
| 22 | 0.29 | 9.62 |
| 23 | 0.41 ± 0.09 | 2.02 ± 0.46 |
| 24 | 1.40 ± 0.61 | 11.45 ± 4.29 |
| 25 | 2.40 ± 0.61 | 11.45 ± 4.29 |
| 26 | 2.24 ± 0.17 | 14.29 ± 2.10 |
| 27 | 0.22 ± 0.03 | 5.04 ± 0.58 |
| 28 | 0.89 | 1.91 |
| 29 | 1.36 | 3.04 |
| 31 | 0.77 | 3.82 |
| 35 | 0.56 | 6.10 |
| 36 | 0.20 ± 0.08 | 3.29 ± 1.02 |
| 37 | 1.78 ± 0.10 | 12.47 ± 1.34 |
| 38 | 5.28 | — |
| 40 | 0.50 | 11.70 |
| 41 | — | 10.30 |
| Compound A | 1.0 | 22.7 |
| Compound B | 80.0 | 833.0 |
| Compound C | 5.4 | 208.0 |
| Compound D | 1.2 | 51.0 |
| Compound E | 6.3 | 66.4 |
| Compound F | 0.8 | 3.8 |

The compounds of the invention also demonstrate excellent activity in an in vivo mu and kappa opioid receptor antagonist test in mice. The procedure used to establish this activity follows.

In order to determine in vivo opioid receptor antagonism, the writhing test, usually used for measuring analgesia, was used with mice. The mouse writhing response was defined as a contraction of the abdominal musculature, followed by the extension of the hind limbs. Writhing was induced by the intraperitoneal administration of 0.6% acetic acid in a volume of 1 ml/100 g of body weight. Five CF-1 male mice (Charles River, Portage, Mich.), weighing approximately 20–22 grams each after being fasted overnight, were observed simultaneously for 10 minutes for the writhing response, beginning five minutes after injection of acetic acid. The percent inhibition of writhing was calculated from the average number of writhes in the control group. Each dose combination was administered to five mice.

Each potential opioid antagonist was administered in various doses with an analgesic dose of morphine, a prototypical mu opioid receptor agonist, and an analgesic dose of U-50,488H, a prototypical kappa opioid receptor agonist. The respective doses were 1.25 and 2.5 mg/kg s.c. These doses produce between 90 and 100% inhibition of writhing. Each potential antagonist was tested at 1.25 mg/kg s.c. with morphine and U-50,488. If there was a significant antagonism of the analgesia of either morphine or U-50,488, then enough subsequent doses of the antagonist would be tested so as to generate a complete dose-response curve and to calculate an antagonist dose-50 ($AD_{50}$). The $AD_{50}$ was calculated from a linear regression equation of probit-plotted data and defines the estimated dose which reduces the analgesic effect of the agonist to 50% inhibition of writhing. Injections of test drugs and the prototypical agonists occurred 20 minutes before the injection of acetic acid.

The results of the foregoing mouse writhing assay are set forth below in Table II. In the Table, column 1 provides the Example Number of the compound evaluated in the assay; column 2, the amount of the compound evaluated in mg/kg necessary to reduce the analgesic effect of the agonist at the mu receptor to 50% inhibition of writhing; and column 3, the amount of the compound evaluated in mg/kg necessary to reduce the analgesic effect of the agonist at the kappa receptor to 50% inhibition of writhing.

TABLE II

| Example No. of Compound Tested | Mouse Writhing Assay Mu $AD_{50}$ (mg/kg) | Kappa $AD_{50}$ (mg/kg) |
|---|---|---|
| 1 | 0.26 | 0.22 |
| 2 | 0.21 | 0.29 |
| 3 | 0.08 | 0.29 |
| 4 | 0.35 | 0.23 |
| 5 | 1.01 | 0.54 |
| 6 | 0.13 | 0.22 |
| 7 | 0.11 | 0.12 |
| 8 | 0.21 | 0.64 |
| 9 | 0.12 | 0.13 |
| 10 | 0.46 | 0.34 |
| 11 | 0.19 | 0.35 |
| 12 | 0.56 | 0.42 |
| 13 | 0.10 | 0.12 |
| 14 | 0.37 | 0.60 |
| 15 | 0.11 | 0.09 |
| 16 | 0.87 | 0.62 |
| 17 | 0.21 | 0.19 |
| 18 | 0.04 | 0.08 |
| 20 | 0.14 | 0.35 |
| 22 | 0.05 | 0.11 |
| 23 | 0.01 | 0.07 |
| 24 | 0.05 | 0.24 |
| 25 | 0.03 | 0.36 |
| 26 | 0.07 | 0.52 |
| 27 | 0.07 | 0.14 |
| 28 | 0.08 | 0.22 |
| 29 | 0.35 | 0.89 |
| 30 | 0.11 | 0.47 |
| 31 | 1.42 | 0.44 |
| 32 | 0.17 | 3.50 |
| 33 | 0.12 | 0.26 |
| 35 | 0.22 | 0.30 |
| 36 | 0.05 | 0.11 |
| 37 | 0.24 | 0.65 |
| 38 | 0.25 | 0.25 |
| 40 | 0.065 | 0.14 |
| 41 | 0.12 | 0.24 |

TABLE II-continued

| Example No. of Compound Tested | Mouse Writhing Assay | |
|---|---|---|
| | Mu $AD_{50}$ (mg/kg) | Kappa $AD_{50}$ (mg/kg) |
| Compound A | 0.05 | 0.92 |
| Compound B | 0.74 | 2.50 |
| Compound C | 0.14 | 4.5 |
| Compound D | 0.16 | 1.38 |
| Compound E | 0.08 | 1.12 |
| Compound F | 0.05 | 0.06 |

It is well documented that marked diuretic effects are derived from the interaction of opioid antagonists with the kappa-opioid receptor of mammals See, e.g., Leander *The Journal of Pharmacology and Experimental Therapeutics* Vol. 224, No. 1, 89–94 (1983). As such, the compounds of the invention were also evaluated in a rat diuresis assay conducted according to the following procedure described by Leander et al. in *Drug Development Research* 4:421–427 (1984) in an effort to further establish the ability of the present compounds to block kappa receptors.

According to this procedure, sixty male Long-Evans hooded rats (Charles River Breeding Laboratories, Portage, Mich.) weighing between about 300 and 500 grams each were housed either individually or in pairs in a temperature-controlled (23° C.) colony room which was illuminated between 6:00 A.M. and 6:00 P.M. Rodent chow and tap water were continuously available except during the measurement of urine output. The animals were used repeatedly, but no more frequently than twice a week.

In determining the antagonist activity of the present compounds, each animal was injected with 0.8 mg/kg of bremazocine, a potent kappa agonist, to induce urination. The animals were then injected with various doses of the test compounds. To measure urine output, the animals were removed from the home cages, weighed, injected and placed in metabolism cages for 5 hr. Excreted urine was funneled into graduated cylinders. Cumulative urine volumes were determined at designated time intervals, usually at 2 and 5 hr after injection.

The compounds which are salt forms were dissolved in distilled water. If necessary, the compounds were dissolved in distilled water with the aid of either a few drops of lactic acid or hydrochloric acid and gentle warming. All injections were s.c. in a volume of 1 ml/kg of body weight. During tests for antagonism, two injections were given, one on each side of the body.

The results of the rat diuresis study are set forth below in Table III. In the Table, column 1 provides the Example Number of the compound tested; column 2, the amount of compound in mg/kg necessary to reduce the urinary output to 50% of the effect produced by 0.08 mg/kg of bremazocine alone two hours after injection of bremazocine and the test compound; and column 3, the amount of compound in mg/kg necessary to reduce the urinary output to 50% of the effect produced by 0.08 mg/kg of bremazocine alone five hours after injection of bremazocine and the test compound.

TABLE III

| Example No. of Compound Tested | Rat Diuresis Assay | |
|---|---|---|
| | $AD_{50}$ (mg/kg) | |
| | Two Hours | Five Hours |
| 3 | 0.27 | 0.39 |

TABLE III-continued

| Example No. of Compound Tested | Rat Diuresis Assay | |
|---|---|---|
| | $AD_{50}$ (mg/kg) | |
| | Two Hours | Five Hours |
| 4 | 0.17 | 0.46 |
| 5 | 1.91 | 0.92 |
| 6 | — | 0.67 |
| 7 | 1.30 | 1.38 |
| 8 | 3.77 | 3.33 |
| 9 | 2.40 | 0.79 |
| 10 | 14.90 | 3.90 |
| 11 | 1.90 | 1.02 |
| 12 | 7.89 | 8.13 |
| 14 | 0.78 | 0.69 |
| 15 | 0.27 | 0.39 |
| 16 | 7.70 | 4.45 |
| 22 | 1.31 | 0.70 |
| 23 | 0.40 | 0.38 |
| 35 | 2.20 | 1.04 |
| 36 | 4.65 | 1.65 |
| 37 | 2.92 | 1.66 |
| 38 | — | 2.00 |
| 40 | 3.78 | 1.44 |
| 41 | 2.70 | 1.90 |
| Compound A | 4.09 | 2.65 |
| Compound E | 2.71 | 3.49 |
| Compound F | 2.17 | 2.45 |

The compounds of the present invention have also been found to have the ability to decrease the amount of food consumed in vivo. The following assay was employed to evaluate the ability of the compounds of the invention to effect food and water consumption of meal fed obese Zucker rats.

According to this procedure, 3–4 month old obese Zucker rats were trained to eat food daily from 8:00 A.M. to 4:00 P.M. only, such that the body weight gain approximates that if the rats were fed ad libitum. These rats were allowed to consume water at all times. Four groups of rats with four rats in each group, two female and two male, were formed. One group served as control for the other three groups each day. Each of the other groups were given a subcutaneous dose of the compound to be evaluated. The test compound was formulated in physiological saline containing 10% dimethylsulfoxide by volume.

Animals remained drug free for 4 days before the next test. Food and water consumption of each rat were measured for the first four hours. A test on one compound was run for three consecutive days. The drug effect was expressed as the percent of the control for that test day.

The results of this test are set forth below in Table IV. In the Table, column 1 gives the Example Number of the compound evaluated; and column 2 provides the $ED_{20}$ in mg/kg, wherein $ED_{20}$ represents the amount of compound evaluated in mg/kg necessary to decrease food consumption 20% during the first four hours of the experiment.

TABLE IV

| Food Consumption Assay | |
|---|---|
| Example No. of Compound Tested | $ED_{20}$ (mg/kg) |
| 1 | 0.08 |
| 2 | 1.25 |
| 3 | 0.29 |
| 4 | 0.05 |
| 6 | 0.33 |
| 7 | 0.34 |
| 8 | 0.44 |
| 9 | 1.25 |

TABLE IV-continued

Food Consumption Assay

| Example No. of Compound Tested | ED$_{20}$ (mg/kg) |
|---|---|
| 10 | 1.25 |
| 11 | 0.15 |
| 13 | 4.56 |
| 14 | 4.47 |
| 15 | 3.65 |
| 16 | >20.0 |
| 17 | 0.31 |
| 18 | 0.07 |
| 20 | 0.91 |
| 21 | 9.37 |
| 22 | 0.78 |
| 23 | 0.05 |
| 24 | 0.12 |
| 25 | 0.13 |
| 26 | 0.35 |
| 27 | 0.04 |
| 28 | 0.12 |
| 29 | 0.31 |
| 35 | 0.08 |
| 36 | 0.05 |
| 37 | 0.19 |
| 40 | 0.11 |
| Compound A | 0.55 |
| Compound B | 3.99 |
| Compound C | 3.72 |
| Compound D | 0.94 |
| Compound E | 1.40 |
| Compound F | 2.05 |

While it is possible to administer a compound of the invention directly without any formulation, the compounds are preferably employed in the form of a pharmaceutical formulation comprising a pharmaceutically acceptable carrier, diluent or excipient and a compound of the invention. Such compositions will contain from about 0.1 percent by weight to about 90.0 percent by weight of a present compound. As such, the present invention also provides pharmaceutical formulations comprising a compound of the invention and a pharmaceutically acceptable carrier, diluent or excipient therefor.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

| | Amount Per Capsule | Concentration by Weight (percent) |
|---|---|---|
| trans-(+)-1-[S-(3-hydroxy-3-cyclohexylpropyl)]-3,4-dimethyl-4-(3-hydroxyphenyl)piperidine hydrochloride | 250 mg | 55.0 |
| starch dried | 200 mg | 43.0 |
| magnesium stearate | 10 mg | 2.0 |
| | 460 mg | 100.0 |

The above ingredients are mixed and filled into hard gelatin capsules in 460 mg quantities.

Formulation 2

Capsules each containing 20 mg of medicament are made as follows:

| | Amount Per Capsule | Concentration by Weight (percent) |
|---|---|---|
| trans-(±)-1-[R-(3-hydroxy-3-cyclohexylpropyl)]-3,4-dimethyl-4-(3-hydroxyphenyl)piperidine | 20 mg | 10.0 |
| starch | 89 mg | 44.5 |
| microcrystalline cellulose | 89 mg | 44.5 |
| magnesium stearate | 2 mg | 1.0 |
| | 200 mg | 100.0 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| | Amount Per Capsule | Concentration by Weight (percent) |
|---|---|---|
| trans-(±)-1-(3-oxo-n-octyl)-3,4-dimethyl-4-(3-hydroxy- | 100 mg | 30.0 |

-continued

|  | Amount Per Capsule | Concentration by Weight (percent) |
|---|---|---|
| phenyl)piperidine hydroiodide |  |  |
| polyoxyethylene sorbitan monooleate | 50 mcg | 0.02 |
| starch powder | 250 mg | 69.98 |
|  | 350.05 mg | 100.00 |

The above ingredients are thoroughly mixed and placed in an empty gelatin capsule.

Formulation 4

Tablets each containing 10 mg of active ingredient are prepared as follows:

|  | Amount Per Capsule | Concentration by Weight (percent) |
|---|---|---|
| trans-(±)-1-(5-methylhexyl)-3,4-dimethyl-4-(3-hydroxy-phenyl)piperidine maleate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
|  | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formula may be prepared using the ingredients below:

|  | Amount Per Capsule | Concentration by Weight (percent) |
|---|---|---|
| trans-(±)-1-[S-(3-hydroxy-3-cyclo-hexylpropyl)]-3,4-dimethyl-4-(3-hydroxyphenyl)piperidine hydrochloride | 250 mg | 38.0 |
| cellulose microcrystalline | 400 mg | 60.0 |
| silicon dioxide fumed | 10 mg | 1.5 |
| stearic acid | 5 mg | 0.5 |
|  | 665 mg | 100.0 |

The components are blended and compressed to form tablets each weighing 665 mg.

Formulation 6

Suspensions each containing 5 mg of medicament per 5 ml dose are made as follows:

|  | per 5 ml of suspension |
|---|---|
| trans-(±)-1-(3-hydroxy-n-hexyl)-3,4-dimethyl-4-(3-hydroxyphenyl)-piperidine hydrochloride | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

|  | Concentration by Weight (percent) |
|---|---|
| trans-(±)-1-[R-(3-methoxy-3-cyclo-hexylpropyl)]-3,4-dimethyl-4-(3-hydroxyphenyl)piperidine hydrochloride | 0.25 |
| ethanol | 29.75 |
| Propellant 22 (chlorodifluoromethane) | 70.00 |
|  | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

We claim:

1. A method of treating a disorder selected from the group consisting of spinal damage, stroke and head trauma in humans comprising administering to a human in need of such treatment an effective dose of a trans-3,4 isomer of a compound of the formula

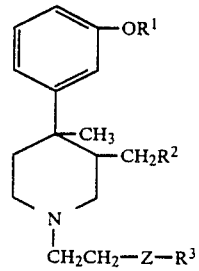

wherein:
$R^1$ is hydrogen or $C_1$-$C_4$ alkanoyl;
$R^2$ is hydrogen, $C_1$-$C_4$ alkyl or $C_2$-$C_6$ alkenyl;

R³ is C₄-C₈ cycloalkyl, C₄-C₈ cycloalkenyl, C₁-C₆ alkyl, C₂-C₆ alkenyl, C₁-C₄ alkyl substituted C₄-C₈ cycloalkyl, C₁-C₄ alkyl substituted C₄-C₈ cycloalkenyl or thiophene;

Z is

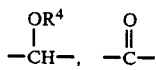

or a bond;

R⁴ is hydrogen, C₁-C₆ alkyl,

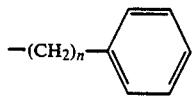

or

R⁵ is C₁-C₄ alkyl or

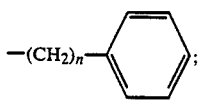

n is 1, 2 or 3; or
a pharmaceutically acceptable salt thereof.

2. The method of claim 1 wherein said disorder is shock.

3. A method of claim 2 wherein R³ is C₄-C₈ cycloalkyl.

4. A method of claim 3 wherein R³ is cyclohexyl.

5. The method of claim 4 which is the (+)-trans isomer

6. The method of claim 5 which is trans-(+)-1-[S-(3-hydroxy-3-cyclohexylpropyl)]-3,4-dimethyl-4-(3-hydroxyphenyl)piperidine.

7. The method of claim 1 wherein said disorder is spinal damage.

8. A method of claim 7 wherein R³ is C₄-C₈ cycloalkyl.

9. A method of claim 8 wherein R³ is cyclohexyl.

10. The method of claim 9 which is the (+)-trans isomer

11. The method of claim 10 which is trans-(+)-1-[S-(3-hydroxy-3-cyclohexylpropyl)]-3,4-dimethyl-4-(3-hydroxyphenyl)piperidine.

12. The method of claim 1 wherein said disorder is stroke.

13. A method of claim 12 wherein R³ is C₄-C₈ cycloalkyl.

14. A method of claim 13 wherein R³ is cyclohexyl.

15. The method of claim 14 which is the (+)-trans isomer.

16. The method of claim 15 which is trans-(+)-1-[S-(3-hydroxy-3-cyclohexylpropyl)]-3,4-dimethyl-4-(3-hydroxyphenyl)piperidine.

17. The method of claim 1 wherein said disorder is head trauma.

18. A method of claim 17 wherein R³ is C₄-C₈ cycloalkyl.

19. A method of claim 18 wherein R³ is cyclohexyl.

20. The method of claim 19 which is the (+)-trans isomer.

21. The method of claim 20 which is trans-(+)-1-[S-(3-hydroxy-3-cyclohexylpropyl)]-3,4-dimethyl-4-(3-hydroxyphenyl)piperidine.

22. A pharmaceutical formulation comprising an effective amount of a trans-3,4 isomer of a compound of the formula

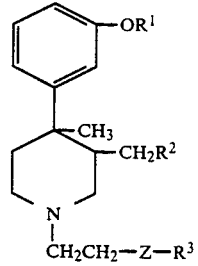

wherein:
R¹ is hydrogen or C₁-C₄ alkanoyl;
R² is hydrogen, C₁-C₄ alkyl or C₂-C₆ alkenyl;
R³ is C₄-C₈ cycloalkyl, C₄-C₈ cycloalkenyl, C₁-C₆ alkyl, C₂-C₆ alkenyl, C₁-C₄ alkyl substituted C₄-C₈ cycloalkyl, C₁-C₄ alkyl substituted C₄-C₈ cycloalkenyl or thiophene;

Z is

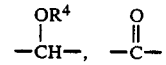

or a bond;
R⁴ is hydrogen, C₁-C₆ alkyl,

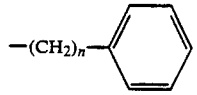

or

R⁵ is C₁-C₄ alkyl or

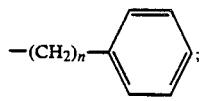

n is 1, 2 or 3; or
a pharmaceutically acceptable salt thereof; and a pharmaceutically acceptable carrier, diluted or excipient therefor.

23. A pharmaceutical formulation of claim 22 wherein R³ is C₄-C₈ cycloalkyl.

24. A pharmaceutical formulation of claim 23 wherein R³ is cyclohexyl.

25. The pharmaceutical formulation of claim 24 which is the (+)-trans isomer

26. The pharmaceutical formulation of claim 25 which is trans-(+)-1-[S-(3-hydroxy-3-cyclohexylpropyl)]-3,4-dimethyl-4-(3-hydroxyphenyl)piperidine.

* * * * *